United States Patent

Jen et al.

[11] Patent Number: 5,951,163
[45] Date of Patent: Sep. 14, 1999

[54] ULTRASONIC SENSORS FOR ON-LINE MONITORING OF CASTINGS AND MOLDING PROCESSES AT ELEVATED TEMPERATURES

[75] Inventors: Cheng-Kuei Jen, Brossard; Ky Thanh Nguyen, Gloucester; Bin Cao, Montreal; Hao Wang, Nun's Island; Chee Ang Loong, Pointe Claire, all of Canada

[73] Assignee: National Research Council of Canada, Ottawa, Canada

[21] Appl. No.: 08/733,113

[22] Filed: Oct. 16, 1996

[51] Int. Cl.[6] .......................... G01K 11/22; G01N 29/18; G01N 29/20

[52] U.S. Cl. ........................... 374/119; 374/139; 73/597; 73/599; 73/644

[58] Field of Search .............................. 73/597, 598, 599, 73/600, 644, 628, 632; 374/117, 118, 119, 139

[56] References Cited

U.S. PATENT DOCUMENTS

| | | | |
|---|---|---|---|
| 3,444,726 | 5/1969 | Young et al. | 73/644 |
| 3,456,715 | 7/1969 | Freedman et al. | 164/155 |
| 3,999,433 | 12/1976 | Japlin | 310/334 |
| 4,509,360 | 4/1985 | Erwin et al. | 73/644 |
| 4,981,045 | 1/1991 | Mountford | 73/644 |
| 5,135,295 | 8/1992 | Cheng-Kuei et al. | 385/13 |
| 5,159,838 | 11/1992 | Lynnworth | 73/644 |
| 5,161,594 | 11/1992 | Bolton et al. | 164/4.1 |
| 5,286,109 | 2/1994 | Hanscombe et al. | 374/119 |
| 5,384,079 | 1/1995 | Bur et al. | 264/21 |
| 5,433,112 | 7/1995 | Piche et al. | 73/597 |
| 5,489,402 | 2/1996 | Knoblauch et al. | 264/407 |
| 5,708,209 | 1/1998 | Stiffler et al. | 73/644 |

FOREIGN PATENT DOCUMENTS

44 40 070  6/1995  Germany.
2 167 185  5/1986  United Kingdom.

OTHER PUBLICATIONS

Digital Real–Time Control of the Die Casting Process Dr. Marcel Loher, Leo Iten.
In Situ Monitoring of Molding Processes Using Laser Based Ultrasound—Addison et al, Rockwell Int. Science Centre, 1049 Camino Dos Rios, Thousand. Oaks, CA 91360 1994.
In–line phase modular using coaxial thick lead zirconate titanate coated optical fibers—D.A. Barrow et al J. Appl. Phys. 79 (6) Mar. 15, 1996.

*Primary Examiner*—Hezron Williams
*Assistant Examiner*—Rose M. Miller
*Attorney, Agent, or Firm*—Marks & Clerk

[57] ABSTRACT

Ultrasonic sensors and associated methods for on-line monitoring of material properties for die casting, molding and extrusion processes at elevated temperatures are disclosed. The sensors include the use of ultrasonic waveguides embedded in the processing machines and piezoelectric ultrasonic transducers. The sensors are operated in the reflection geometry in which one side access of the processing machines is required. The monitoring parameters are the flow front, gap development and temperature of the materials being processed and filled in the cavities of the die in casting processes and the mold in injection molding, and the temperature and viscosity of the molten polymers in the polymer extrusion machines. Piezoelectric ultrasonic transducers made of high Curie temperature materials, fabricated by sol-gel techniques and directly deposited on top of the ultrasonic waveguides or the external walls of the shot sleeve of the die caster, die of the die caster, mold of the injection molding machine or barrel of the extruder are also used.

21 Claims, 10 Drawing Sheets

ULTRASONIC SENSORS FOR ON-LINE MONITORING OF CASTINGS AND MOLDING PROCESSES AT ELEVATED TEMPERATURES

BACKGROUND OF THE INVENTION

1. Field of Invention

This invention relates to ultrasonic devices and methods for on-line monitoring of industrial materials during die casting, molding and extrusion processes at elevated temperatures.

The monitoring properties during processing are the surface disturbance of the molten metals and solidified particles in the shot sleeve of the die caster, flow front, shrinkage and temperature of the processed part in the cavities of the die casting and molding machines, and viscosity and temperature of the extruded polymers. These properties can then be used as the process control parameters for the process optimization. The ultrasonic devices for the monitoring are solid ultrasonic waveguides, also called buffer rods, which are inserted into the processing devices such as the shot sleeve of the die caster, die of the die caster, mold of the injection molding machine or barrel of the extruder, and piezoelectric ultrasonic transducers made of high Curie temperatures and directly deposited on the external surfaces of the shot sleeve, die, mold and barrel by a sol-gel technique. These ultrasonic devices are operated in the reflection geometry in which only one side access of the processing machines is necessary.

2. Description of the Prior Art

In the process of die casting, firstly metal is heated, melted and conveyed to the shot sleeve which is a container, through the runner which is a flow channel and the gate. It is then fed into the cavity of a die which has a unique shape for a designed production part. After filling, the part is cooled and solidified inside the die until it is ejected out at some stage and another run starts.

When the molten metal is in the shot sleeve, little surface disturbance and solidification should exist before the injection. Such a surface disturbance and solidification may significantly degrade the quality of the cast product.

Then the molten metal is injected by the hydraulic cylinder (plunger or piston) into the die cavities through the runner and the gate, the flow of the molten metal advances with certain paths inside the die. Usually, a high pressure is applied through the plunger and the molten metal fills the cavity at a high speed with a strong force. When the cavity is filled, the filling pressure should be immediately switched to a much higher intensification pressure. With the monitoring of the advancement of the flow front a smooth transition from the filling stage to intensification stage can be achieved by switching the filling pressure to a relatively high intensification pressure.

After the filling stage, the part is subjected to an intensification pressure through the gate as it is cooled and solidified. For the die casting process, the gate is frozen soon after the filling, and intensification could be applied right after gate solidification. The ability to detect whether the runner or gate is frozen or solidified or not will help to establish the effectiveness of intensification and thus feeding in the cavity.

When the solidified material begins to shrink through its thickness, a gap is likely to be formed between the die wall and the cast part. Due to the formation of the gap, there might be a significant thermal contact resistance between the part and the cavity wall, and it can reduce the heat transfer efficiency which affects the production cycle. Detection of the gap formation may provide more information about the heat transfer inside the parts and improve the physical understanding of thermal contact resistance of the gap. Furthermore, the detection of the gap can also reveal the uniformity of the cooling throughout the part which is also an important issue affecting the part quality.

In order to increase the production speed the cast part in the die needs to be cooled efficiently and properly in order that it can be ejected in the shortest allowable time frame. Thus, it is desirable to know the temperature and the temperature profile of the cast part in the die cavity and cooling mechanism of the die. This information can help cooling line design, ejection time prediction, etc. In order to probe the temperature profile of the cast part in the cavity of the die three information; namely the surface temperature, the heat flux and the average temperature of the part, are required. One single sensor which can obtain these three information is highly desired.

Therefore, there are four essential monitoring tasks desired to improved the die casting process. They are (a) surface disturbance and solidification monitoring when the molten metal is in the shot sleeve before injection, (b) flow front monitoring during the filling stage, (c) monitoring of the gap development which is caused by the shrinkage of the part during the cooling and (d) monitoring of the temperature of the part that significantly affects the properties such as the warpage, shrinkage and density distribution of the cast part. Performing all these monitoring can lead to an improved on-line quality control system and improve the basic understanding of the die casting process.

In pressure die casting, German Patent, "Sensoreinhelt", DE 44-40-070 A1, Jun. 22, 1995 proposes a device for detecting metal flow based on an electrical contact between two electrodes separated by an insulating ceramic ring making up the metal flow sensor. Once the metal flow passes these two electrodes, the electrical resistance sharply decreases, and hence flow can be detected. This sensor can not be used to measure the flow front of an insulator such as polymer. An improved sensor which overcomes the above problem and carries out other monitoring tasks such as gap development, temperature and viscosity of the cast part is highly desired.

Using pressure sensors which monitor the cavity pressure to detect the gap can be one approach. The onset of gap corresponds to the instant when the pressure drops to zero. However, a precise detection can hardly be achieved because the pressure sensors are made to measure the peak pressures and significant errors may occur, particularly in the low pressure range which corresponds to the critical period when the gap starts to be formed.

In squeeze casting which is a type of die casting the turbulence of the molten metal in the shot sleeve and gas entrapment in the cast part can be significantly reduced. The above four desired monitoring tasks are still desired for the improvement of the casting.

Semi-solid metal casting is another modern type of die casting. It involves injection of, for instance, aluminum alloy in the form of semi-solid slugs (60% solid, 40% liquid) having a consistency of toothpaste into a die cavity. Since semi-solid metal casting operates at about 100° C. lower temperature than the normal casting in which the metal is completely molten, it uses less energy and suffers only a fraction of the solidification shrinkage. For this casting ultrasonic monitoring tasks mentioned above are also desired for the improvement of the process.

Bolton et al. (U.S. Pat. No. 5,161,594, Nov. 10, 1992) reported a tie bar monitoring system using ultrasound for a die casting machine. This previous art is comprised of an ultrasonic device that monitors changes in tie bar length. Such an ultrasonic system will sound an alarm and/or shut down the die cast machine if bending in individual tie bar exceeds a predetermined limit. Such a system cannot perform the desired tasks mentioned above for die casting of metals.

It is understood that polymer injection molding is very similar to the die casting of metals except the material processing temperature is lower. For instance, in the die casting of aluminum and magnesium alloys, the melt temperature of these alloys is in the range of 650–750° C. and that of the polymer in the injection molding is below 350° C. However, there are some differences. For instance, in polymer injection molding machines there is no similar container like shot sleeve in the die casting machines but there is a polymer extrusion process before the injection of polymers. Therefore there are still four essential monitoring tasks for the polymer injection molding.

For the polymer extrusion process L. Piché et al (U.S. Pat. No. 5,433,112, Jul. 18, 1995) discloses the application of ultrasound to characterize a polymer flow. In this previous art the measurement geometry is in the transmission mode for which two side accesses of the extruder are required and only longitudinal waves are used for the measurements. Because the screw of the extruder blocks the transmitted ultrasonic energy, in the monitoring can be only carried out at the exit of the extruder.

Furthermore, after the filling the pressure should be immediately switched to a much lower packing pressure in order to avoid the part splashing in the polymer injection molding. In die casting, the pressure in the cavity is normally increased during the solidification, that is called intensification, to allow more material to enter the cavity in order to compensate for volumetric shrinkage. However, in each case, after the gap is developed, and especially after the gate is frozen, the holding pressure will not further affect the part. Thus keeping the holding pressure through the gate is not necessary. A dynamic control of the hold time of injection molding and die casting may be achieved by monitoring the gap development at the gate location resulting in parts with a higher quality (denser, less porosity, etc.) and an optimal production cycle time. In addition, temperature profile of the part is also an important information for the process control of polymer injection molding.

The above information is also desired for gas assisted injection molding and co-injection molding. In the gas assisted injection molding a gas is injected into the core of the molded part which consists of a hollow core and an outer layer in order to reduce the material used and the weight, and preserve the desired shape of the part because of the reduced shrinkage. In co-injection molding a low cost material is injected as the core material. For these two injection molding processes the flow front of the gas and core material are also desired to be monitored.

A. J. Bur et al (U.S. Pat. No. 5,384,079, Jan. 24, 1995) discloses used an optical method to detect the thermodynamic phase transitions during polymer injection molding. This optical method not only needs to add a fluorescent dye which is a foreign material into the mold but also use glass optical fibers as the detectors of which the thermal characteristics are different from that of the mold material which is generally steel. A sensing mechanism which does not add foreign material, has same thermal characteristics as the mold and performs the desired three monitoring tasks is highly desired.

The ability of the ultrasound to interrogate noninvasively, nondestructively and rapidly the surface and internal regions of material objects is clearly desirable for a modern injection molding process control. Such a control should not disturb normal processing conditions and consistent product properties in a batch or continuous process and, at the same time, it should acquire the desired information fast enough to provide efficient feedback to the process control. Recent advances in transducer materials, microprocessors, digital signal processing and measurement techniques allow the data to be obtained and analyzed rapidly, reliably and economically, and make ultrasound a practical tool for on-line production monitoring.

In the publication "In situ monitoring of molding processes using laser-based ultrasound", Review of Progress in Quantitative Nondestructive Evaluation, vol. 13, Plenum Press, New York, pp.2237–44, 1994, Addison, Jr. et al recognized the capability of ultrasound and reported a laser ultrasonic method to monitor the flow front of the molten polymer in a compression molding and a resin transfer molding machines. This laser ultrasonic method is non contact. However, the repetition rate of the high power laser pulses which generate ultrasound in the material is around 100 Hz which is too slow for the monitoring of the flow front and the gap development in the metal die casting and polymer injection molding machines.

SUMMARY OF THE INVENTION

According to the present invention there is provided an apparatus for monitoring molten material during die casting, molding, extrusion or like processes, comprising an array of ultrasonic transducers operable in the reflection mode, means for ultrasonically coupling said transducers to the molten material, means for energizing said transducers so that they emit pulses of ultrasonic energy into the molten material, means for receiving return pulses from said transducers, and a processing means for analyzing said return pulses to derive data therefrom pertaining the state of the molten material.

According to the one embodiment of the invention, there are provided ultrasonic devices operated in the reflection mode and used to monitor the molten metals in the shot sleeve prior to the injection, and the flow front, temperature and gap development of the metals being processed in the cavities of the die in die casting of metals.

According to the another embodiment of the invention, there are provided ultrasonic devices operated in the reflection mode and used to monitor the viscosity and temperature of the polymer during polymer extrusion in the extruder prior to the injection, the flow front, temperature and gap development of the polymers being processed in the cavities of the mold in injection molding of polymers.

According to the another embodiment of the invention, there is provided an ultrasonic monitoring system consisting of a solid elongated ultrasonic waveguide embedded into the cast, molding or extrusion machine for transmitting ultrasonic waves, generated, e.g. by a transducer into a cast, molded or extruded molten material and reflected from that material. The buffer rod is made of a low loss ultrasonic material. The buffer rod can be a clad buffer rod consisting of a core and a cladding providing good ultrasonic wave guidance in the core.

According to the another embodiment of the invention, there is provided an ultrasonic monitoring system consisting of a piezoelectric high temperature (>300° C.) ultrasonic transducer which is fabricated by sol-gel processing of thick (>200 μm) piezoelectric material directly on top of the buffer rod or the external wall of the die, mold or extrusion machines.

The invention also provides an apparatus, wherein said buffer rods are provided with longitudinally spaced means to reflect said pulses, at the end thereof coupled to the molten material, and said computer is programmed to calculate the travel times of the pulses reflected from said longitudinally spaced means the velocity of said pulses in said buffer rods and derive therefrom the temperature of the end of the rod containing said longitudinally spaced means.

When ultrasonic waves impinge at the boundary between two different media, some of the energy is transmitted through the boundary and the rest is reflected back. The reflection and transmission coefficients, R and T, are respectively:

$$R = \frac{Z_1 - Z_2}{Z_1 + Z_2} \qquad (1)$$

where $Z_i$ is the acoustic impedance of medium i which is defined as the product of the density $p_i$ and wave velocity $V_i$ of the materials:

$$Z_i = p_i V_i (i=1,2) \qquad (3)$$

Pulse-echo ultrasonic measurements in this invention are operated in reflection geometry in which the signal is transmitted and received by the same ultrasonic transducer (UT). Only one side access of the processing machine is needed. In transmission geometry, signal is transmitted by one UT and received by another and it is often limited in practical use because of the requirement of the installation of two UTs on the two sides of the processing machines.

BRIEF DESCRIPTION OF THE DRAWINGS

The invention will now be described in more detail, by way of example, only with reference to the accompanying drawings, in which:

FIG. 9(a) showing the empty cavity before casting FIG. (b) showing good contact after casting and FIG. 9(c) showing loss of contact after gap formation;

DETAILED DESCRIPTION OF THE PREFERRED EMBODIMENTS OF THE INVENTION

Figure 1:
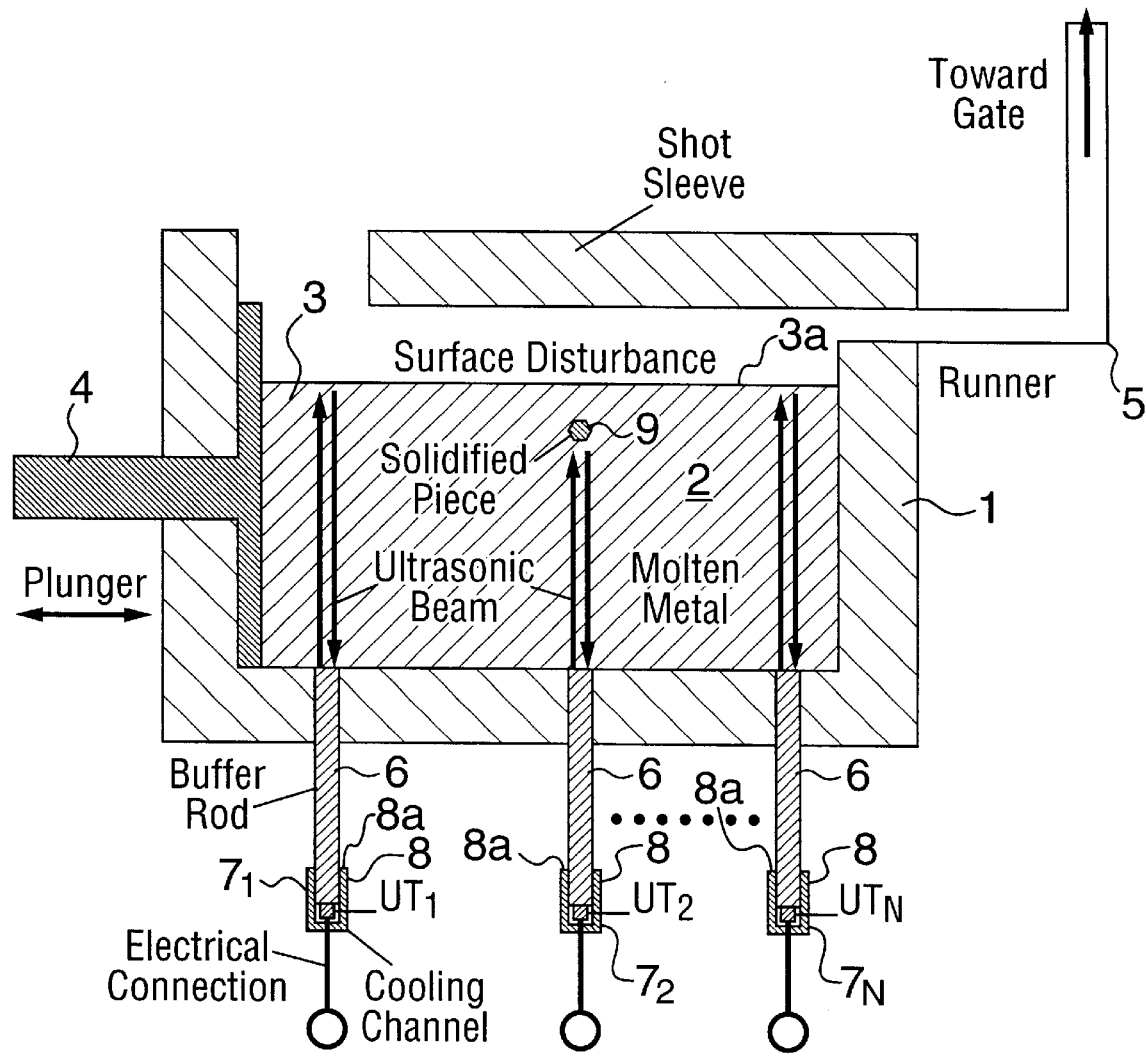
FIG. 1 is a diagrammatic sectional view of a shot sleeve showing a measurement configuration which uses the ultrasound to measure the surface disturbance and detect the solidified particles inside the shot sleeve.

The apparatus shown in FIG. 1 comprises a shot sleeve 1 defining a cavity 2 containing molten metal 3. A plunger 4 is used to eject molten metal through runner 5 to the gate (not shown). A series of buffer rods 6 acting as waveguides extend through the bottom of the slot sleeve 1 and come into contact with the molten metal 2.

Ultrasonic Transducers (UTs) $7_1, 7_2, \ldots 7_n$ forming a linear array are located at the free ends of the buffer rods 6 within cooling jackets 8.

Solidified pieces of metal 9 can form within the molten metal 3.

FIG. 1 shows a measurement configuration which uses the ultrasound to measure the surface disturbance and detect the solidified particles 9 inside the shot sleeve 1. When ultrasound is launched from the UTs 7 and propagates through the ultrasonic waveguide also called buffer rod attached to the UT 7 by a thin layer of ultrasonic couplant, a part of its energy will be reflected from the buffer rod-molten metal interface and the rest will be transmitted into the molten metal in the shot sleeve. The buffer rod is embedded in the shot sleeve as shown in FIG. 1.

The UTs 7 can be of the longitudinal or shear wave type. The transmitted ultrasound in the molten metal will be reflected if it meets the solidified particle and the top surface where there is the molten metal-air interface and a total reflection happens at this interface.

The buffer rods 6 and UTs 7 thus constitute an array of N ultrasonic probes which consist of N buffer rods and UTs; which can be used to monitor many desired locations at the same time.

Figure 2:
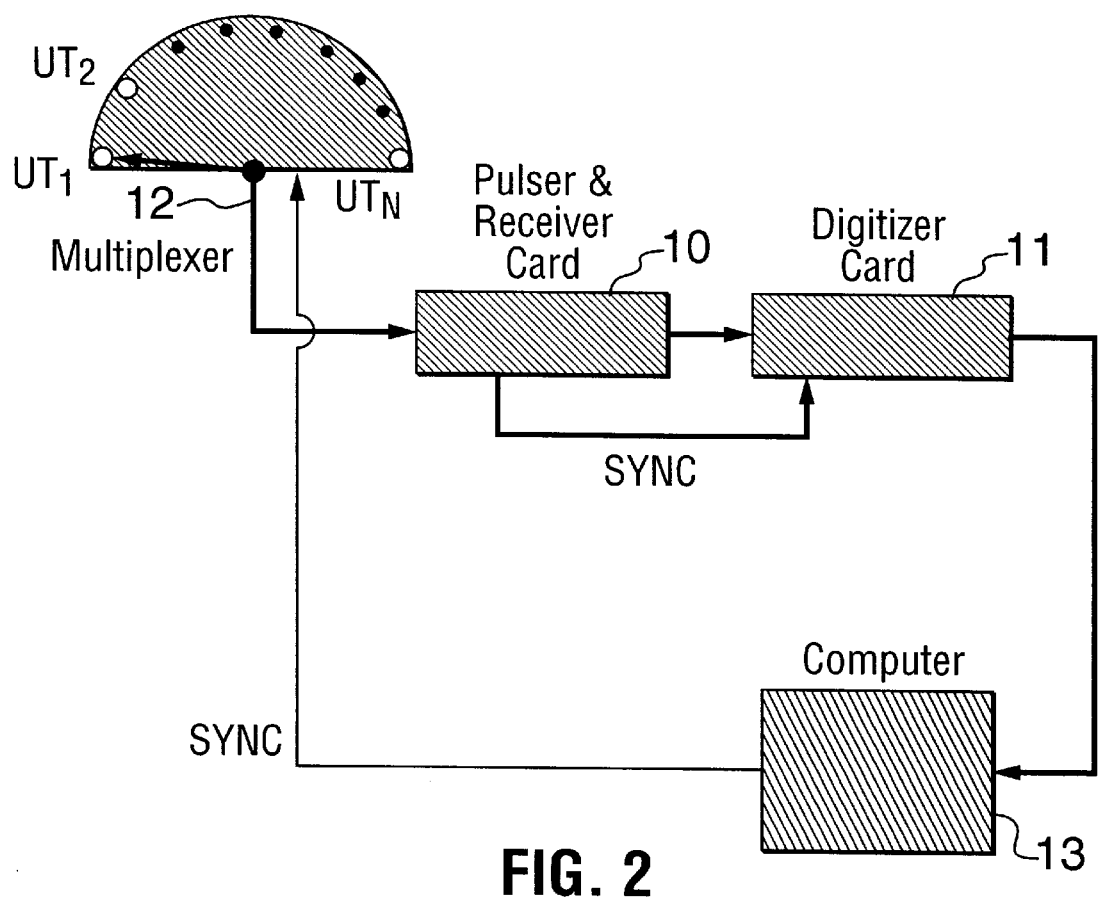
FIG. 2 is a schematic of the electronics system for ultrasonic monitoring.

A schematic of the electronic system which consists of a pulser and receiver card 10, a digitizer card 11, a multiplexer 12 and a computer 13 for the ultrasonic monitoring is depicted in FIG. 2.

The pulser and receiver card 10 generates the electrical signal to drive the UTs 7 and receives the signal containing the desired information from the same UT 7. The digitizer card 11 digitizes the analog signal from the receiver 10 for the purpose of data acquisition, signal processing and display carried out in the computer 13.

The multiplexer 12 shown in FIG. 2 is a fast switch in order to scan from UT $7_1$ to UT $7_n$ shown in FIG. 1. The switching time from one channel to the other is in the order of milli-seconds and n can be more than 40. All handling of the electrical signals can be synchronized by the SYNC signal provided by the pulser card 10 in the computer 13.

Since the materials are processed at elevated temperatures, for instance, above 300° C., and economical and high performance UTs and couplants can be only reliably operated at a temperature below 50° C., a cooling mechanism together with each UT attached to each buffer rod is used. One side of the buffer rod contacts the melt which is about 750° C. for aluminum and another side is cooled by a cooling channel 8a formed in cooling jacket 8 using high pressure air or water such that the temperature at the UT location is below 50° C. A thin layer of ultrasonic couplant, normally gel with very high viscosity, is laid between each UT and the cooling end of the buffer rod.

The operation frequency of UTs 7 is commonly in the range of 0.5–30 MHz. The high frequency end is limited by the large ultrasonic loss in the molten material to be monitored and the low frequency end is confined by the size and the efficiency of the UT.

Figure 3:
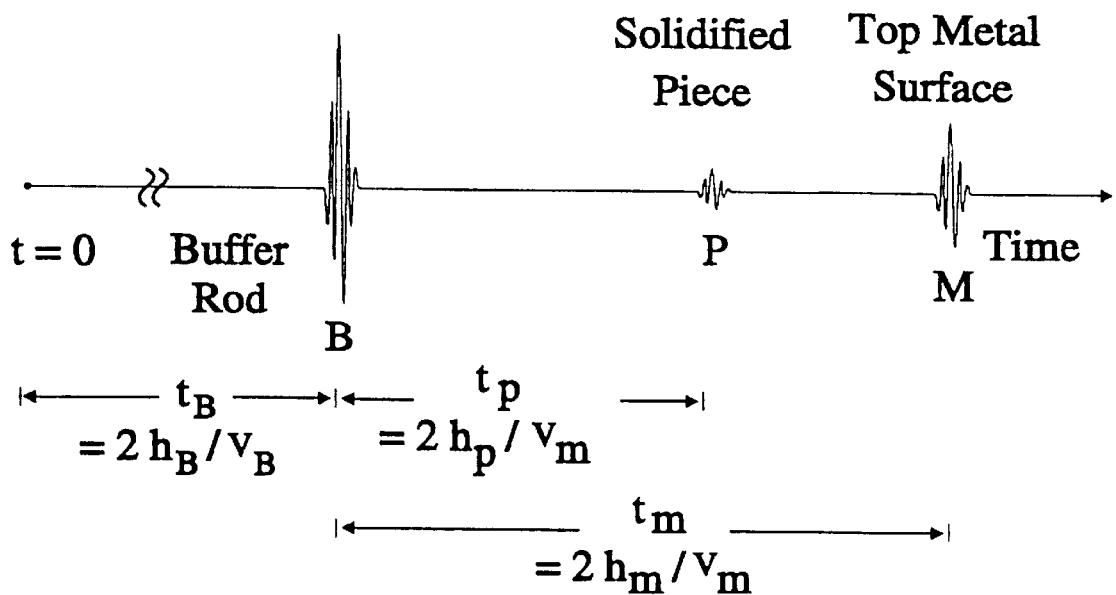
FIG. 3 is a schematic of the reflected ultrasonic longitudinal wave signals corresponding to the reflections from the end of the buffer rod, solidified particle and the top surface of the molten metal for each ultrasonic probe embedded in the shot sleeve.

FIG. 3 shows a schematic of the corresponding ultrasonic signals received from each longitudinal UT 7 and the time delays in FIG. 1. In FIG. 3, $V_B$ and $V_m$ are the ultrasonic longitudinal velocity of the buffer rod 6 and molten metal 3 respectively; $h_B$ and $t_B$ are the length of the buffer rod 6 and ultrasonic round trip travel time in the buffer rod 6 respectively. Also $h_p$ & $t_p$ and $h_m$ & $t_m$ are the distance and ultrasonic round trip travel time measured from the end of the buffer rod 6 to the location of the solidified particle 9 and the molten metal-air interface 3a respectively. Since $t_B$, $t_p$ and $t_m$ are in the range of tens of microseconds and a switching time from one monitoring channel to the other is in the range of milli-seconds, the ultrasound can be used to monitor the surface disturbance and the solidified particle 9 in the shot sleeve 1 during the process.

Since such surface disturbance and solidification significantly degrade the quality of the cast product, the monitoring results can be used for obtaining optimal process parameters such as temperature of the shot sleeve and plunger moving speed.

Figure 4:
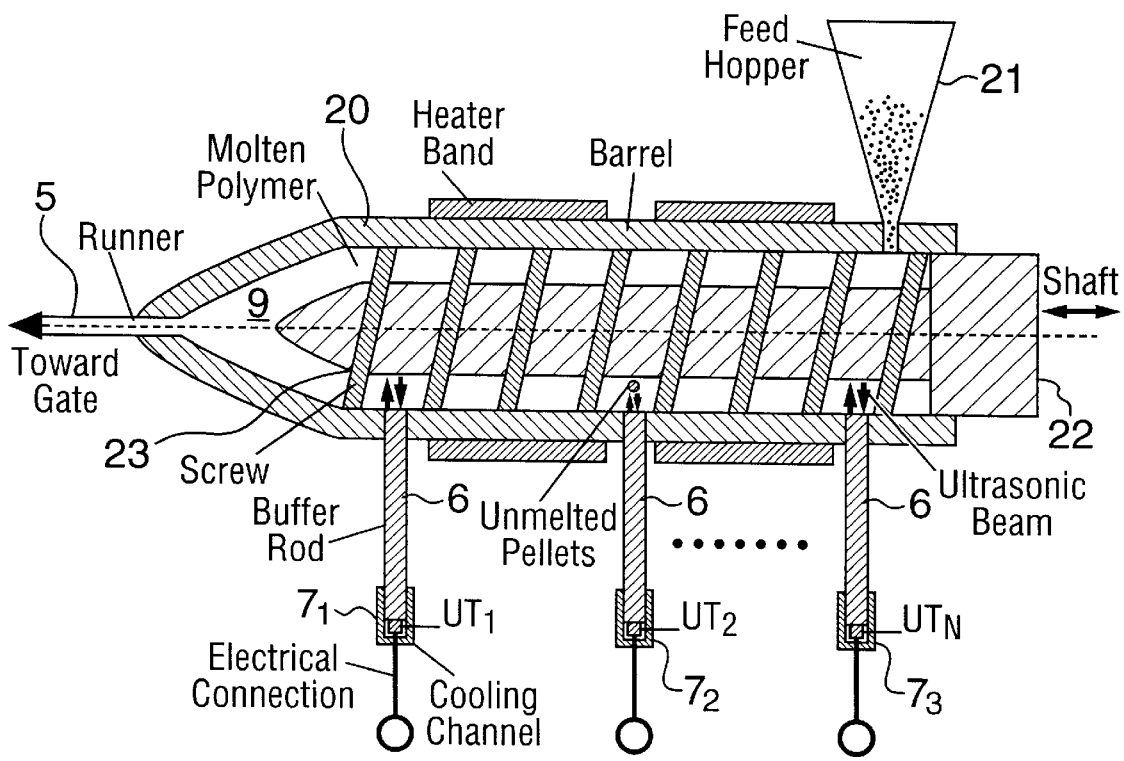
FIG. 4 is a sectional diagrammatic view of a barrel extruder, showing a measurement configuration which uses the ultrasound to measure the polymer property and detect the unmelted particles inside the extruder, the ultrasonic waveguides being embedded in the barrel of the extruder.

FIG. 4 shows an arrangement which uses the ultrasound to measure the polymer property and detect the unmelted pellets inside the extruder along the extrusion direction.

The arrangement includes a barrel extruder 20 with a feed hopper 21 and an axial shaft 22 supporting an archimedes screw 23 for urging molten polymer 3 toward the runner 6. The buffer rods $7_1, 7_2, \ldots 7_n$ are embedded in the barrel of the extruder.

In operation, the reflection mode is used, and monitoring of whether the polymer is undergoing proper processing at different locations along the shaft during extrusion is carried out using multiple probes shown in FIG. 4 and the multiplexer 12 shown in FIG. 2.

Figure 5:
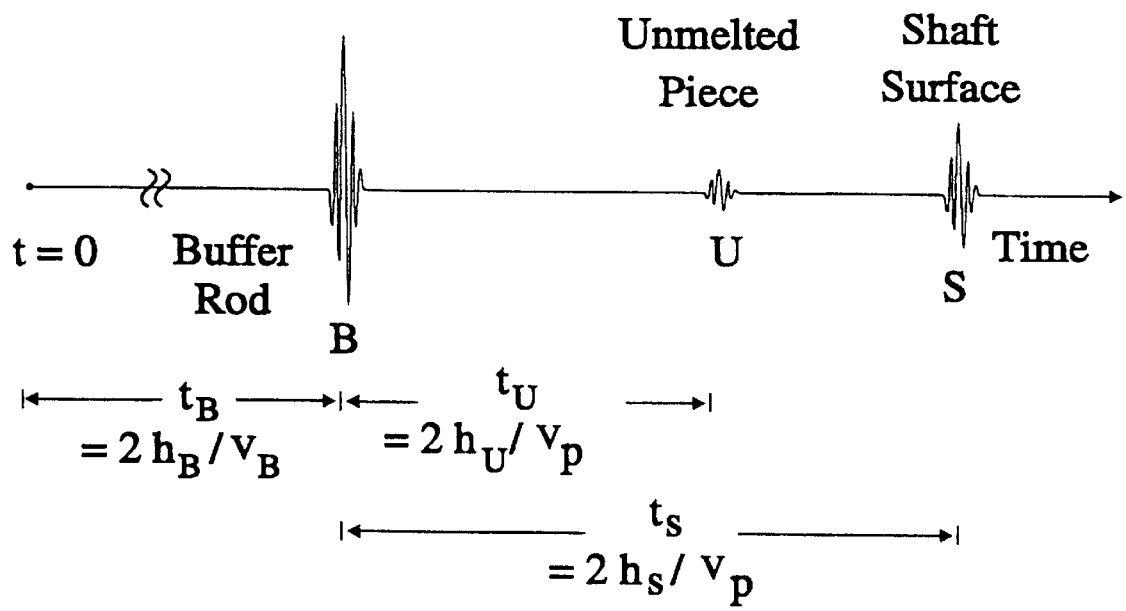
FIG. 5 is a schematic of the reflected ultrasonic longitudinal wave signals corresponding to the reflections from the end of the buffer rod, unmelted particle and the surface of the shaft for each ultrasonic probe embedded in the barrel of the extruder.

FIG. 5 shows a schematic of the corresponding ultrasonic signals received from each UT and the time delays in FIG. 4. In FIG. 5, $V_p$ is the ultrasonic longitudinal wave velocity of the molten polymer; $h_U$ & $t_U$ and $h_p$ & $t_p$ are the distance and ultrasonic round trip travel times measured from the end of the buffer rod to the location of the unmelted pellets and the molten polymer-shaft interface respectively. Since the longitudinal velocity $V_p$ and attenuation in the molten polymer is a function of the viscosity of the polymer, the measurement of the velocity $V_p$ and attenuation can derive the information of viscosity of the molten polymer. Again, since $t_U$ and $t_p$ are also in the range of tens of microseconds and a switching time from one monitoring channel to the other in the range of milliseconds, the ultrasound can be used to monitor the property such as viscosity and the unmelted pellets in the extruder during the process.

Shear waves can be launched and received in the reflection mode. Although the attenuation of the shear waves in molten materials is high, however, if the thickness of the part is thin the ultrasonic shear wave signals at low MHz frequency range with enough signal to noise ratio can still be obtained for monitoring purposes.

Figure 6:
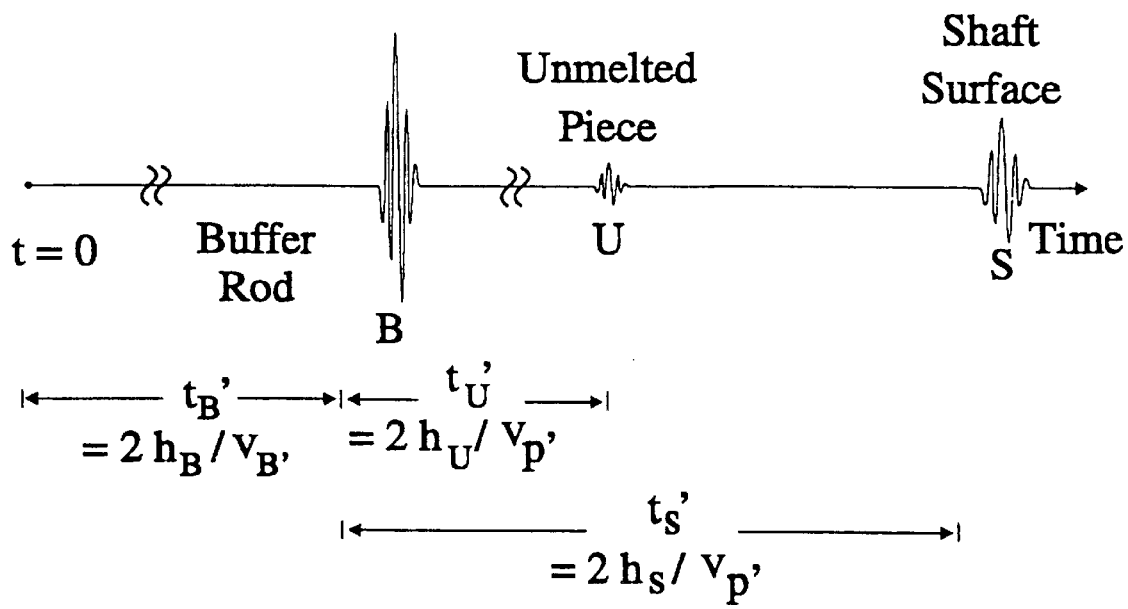
FIG. 6 is a schematic of the reflected ultrasonic shear wave signals corresponding to the reflections from the end of the buffer rod, unmelted particle and the surface of the shaft for each ultrasonic probe embedded in the barrel of the extruder.

FIG. 6 shows a schematic of the corresponding ultrasonic shear signals received from each shear wave UT and the time delays in FIG. 4. In FIG. 6, $V_{B'}$ and $V_{p'}$ are the ultrasonic shear wave velocity of the buffer rod and molten polymer respectively; $t_B{}'$ is the ultrasonic round trip travel time for the shear wave in the buffer rod; also $t_U{}'$ and $t_p{}'$ are the ultrasonic shear wave round trip travel time measured from the end of the buffer rod to the location of the unmelted pellets and the molten polymer-shaft interface respectively. Again since the shear velocity $V_{p'}$ and its attenuation of the molten polymer is also a function of the viscosity of the polymer, the measurement of the velocity $V_{p'}$ and attenuation can derive the information of viscosity of the molten polymer. In addition, since $t_B{}'$, $t_U{}'$ and $t_p{}'$ are in the range of tens of microseconds and a switching time from one monitoring channel to the other is in the range of milli-seconds, the ultrasound can be used to monitor the property such as viscosity and the unmelted pellets in the extruder during the process.

Figure 7:
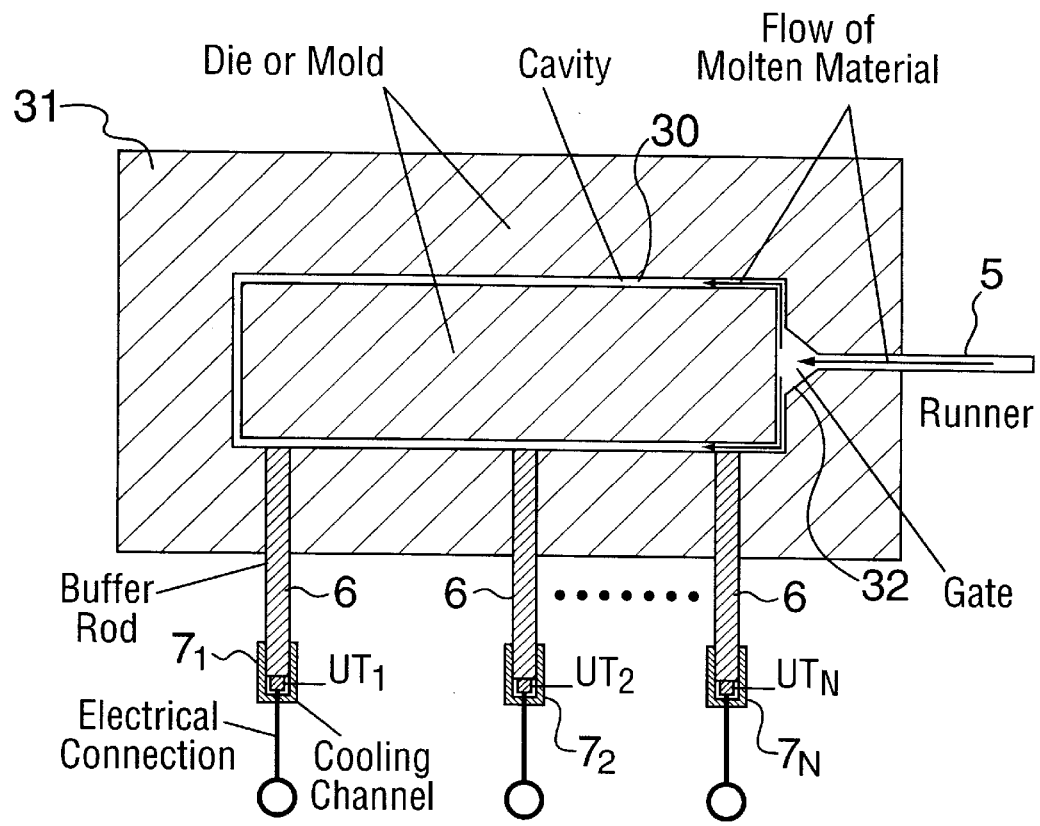
FIG. 7 is a sectional diagrammatic view of a die mold showing a measurement configuration which uses the ultrasound to measure the flow front and gap development inside the cavity of a die or mold in which the ultrasonic waveguides are embedded.

FIG. 7 shows a die or mold, which may be gas assisted. After the molten metal is filled into the shot sleeve 1 or molten polymer is melted in the extruder 20, these molten materials will be injected by the hydraulic cylinder (plunger or piston) into the die cavity 30 of a die caster or mold cavity of an injection molding machine 31 through the runner 5 and the gate 32 as shown in FIG. 7. They advance with certain paths inside the cavities of the die or the mold. Due to the necessary cooling mechanism provided by the die or the mold these molten materials will be solidified and shrunk, and then gaps are developed between the solidified part and the wall of the die or mold.

Figure 8:
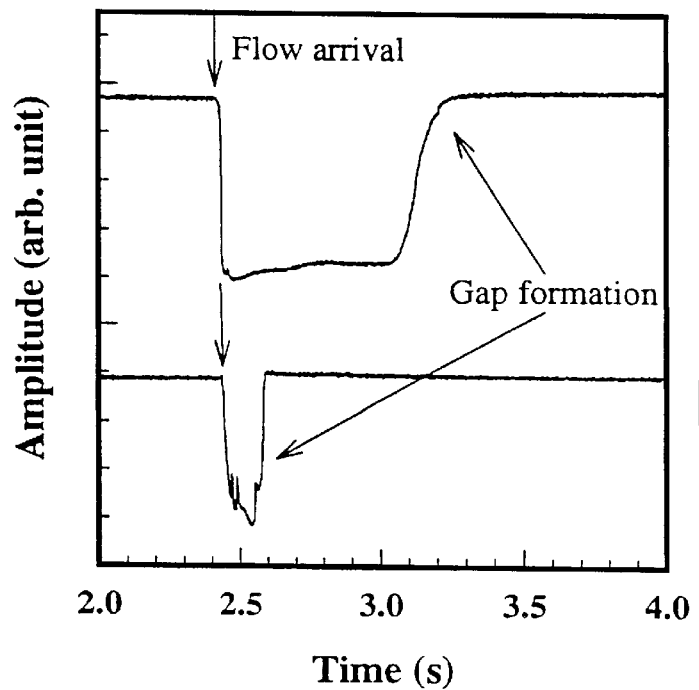
FIG. 8 shows the amplitude variation of the reflected signal at the buffer rod-part interface in flow front and gap development monitoring for the die-casting of aluminum.

FIG. 8 shows the flow front and gap development monitoring for a die-casting of aluminum process in our invention, and the amplitude variation of the reflected signal at buffer rod-part interface is used.

Figure 9A:
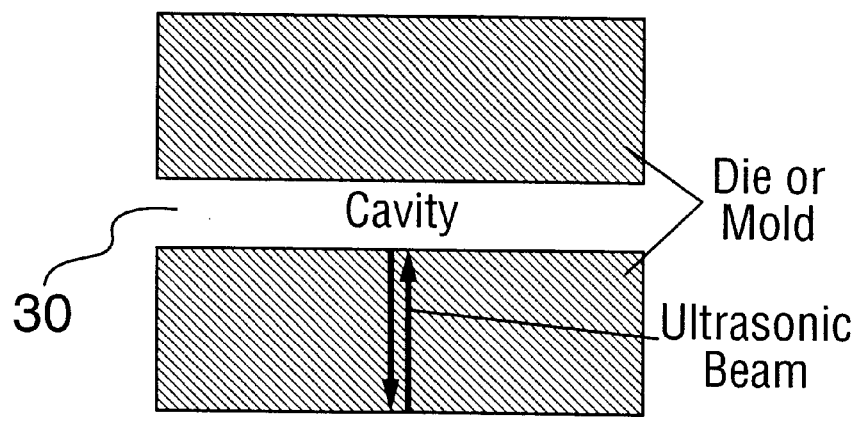
FIGS. 9a–9c illustrates the ultrasonic monitoring of flow front and gap development in reflection mode.
Figure 9B:
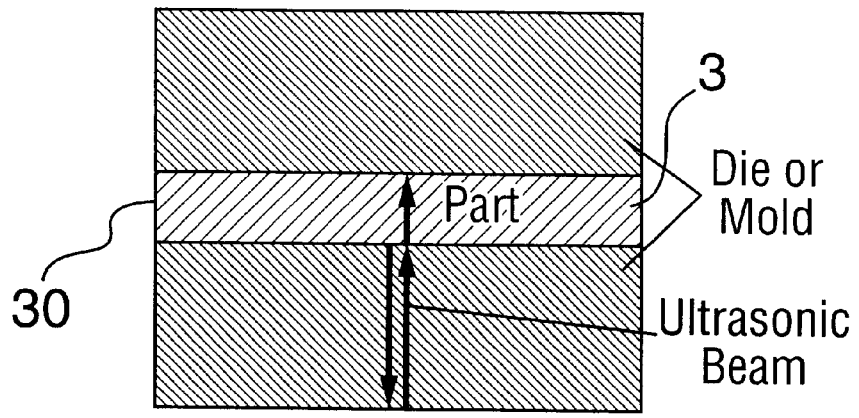
Figure 10:
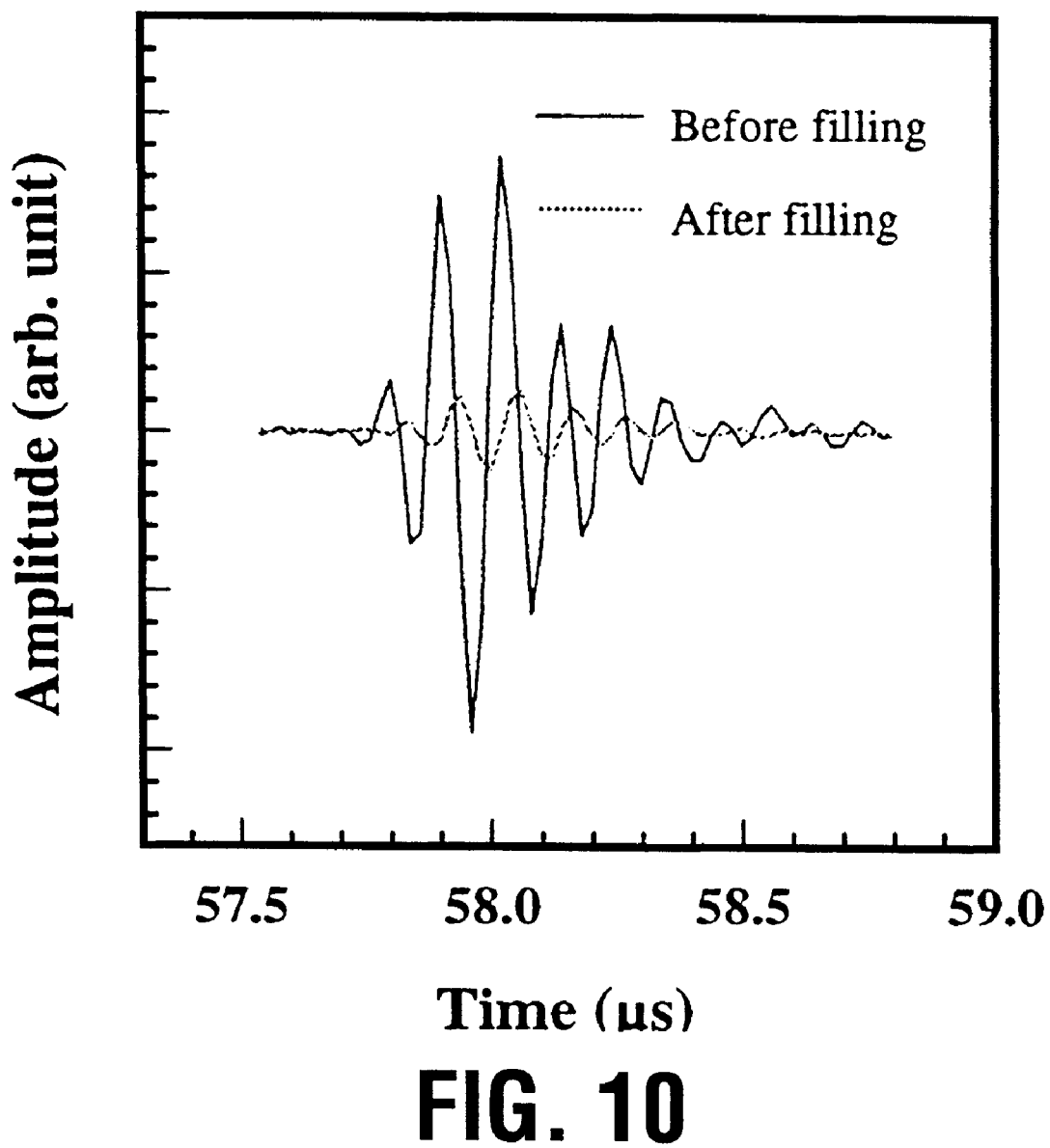
FIG. 10 shows the amplitude variation of the reflected signal at the buffer rod-part interface before and after the filling of the molten aluminum.

Before injection of the molten materials 3 into the die as shown in FIG. 9a, the ultrasonic signal propagating along the buffer rod 6 is totally reflected back from the steel buffer rod-air (cavity) interface due to the very small acoustic impedance of air compared to that of steel. Thereby, the reflection coefficient is nearly 1. During the filling, the flow front advances inside the cavity. As soon as the molten materials wet the buffer rod where the ultrasonic waves impinge as shown in FIG. 9b, a part of the ultrasonic wave energy penetrates into the molten material. The reflected ultrasonic wave amplitude thus decreases accordingly indicating the arrival of the flow front at that particular location as shown in FIG. 10. Using an array of UTs 7 at different locations as shown in FIG. 7, flow front advancement inside the cavity can be obtained.

In FIG. 8 the flow of the molten aluminum arrived at the sensor for obtaining the upper curve earlier than the sensor for obtaining the lower curve. Since the ultrasound can penetrate through the molded part, such a flow front monitoring can be also carried out for gas-assisted injection molding in which a gas is formed as the hollow core for the molded part. The reflected ultrasonic echo at the part-hollow core interface may be used for the monitoring. Thus, not only the flow front of the polymer which forms the outer frame of the molded part but that of the gas may be monitored simultaneously. The attraction of gas-assisted injection molding is that the molded part is light due to the hollow core which also reduces the required material and production cost. The hollow core also decreases the shrinkage of the thick polymer parts, therefore it can minimize the shape distortion caused by the excessive shrinkage.

Similarly during the co-injection molding process in which two materials namely one as the core and another as the outer frame are injected into the cavity of the mold at the same time, the flow front of the both materials may be monitored because the ultrasound can penetrate the outer frame and the reflected ultrasonic echo at the interface between the outer frame and the core material may be used for monitoring. The attraction of the co-injection molding is that the core material can be the low cost such as the recyclable material which may reduce the production cost.

Figure 9C:
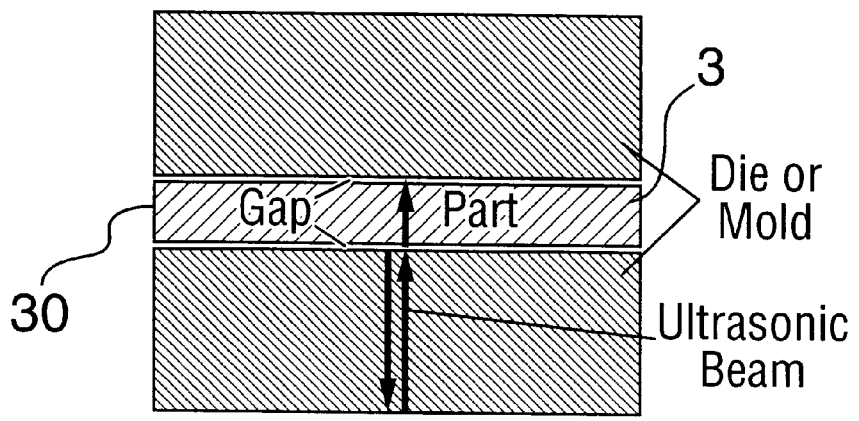

After the filling, the part cools down and then becomes solidified. At the beginning of the solidification, the ultrasonic signal amplitude changes slightly due to minor change of the elastic properties of the part. As the solidification progresses, the part begins to shrink through its thickness and a gap is likely to be formed (FIG. 9c). After a gap is developed, the sensed interface corresponds to the steel buffer rod-air condition, therefore, the reflected amplitude returns to the maximum level. In FIG. 8, the thickness of the cast aluminum plate was thicker for the upper curve, thus took longer time for the gap development.

Figure 11A:
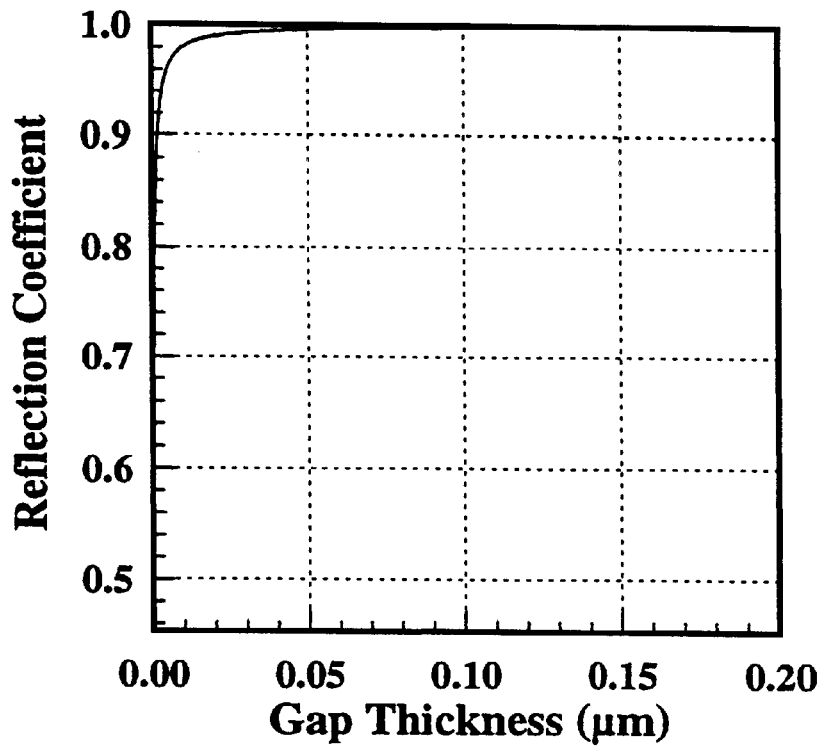
FIGS. 11a to 11b show the calculated reflection coefficients for the (a) steel-air-cast aluminum and (b) steel-air-injected polymer as a function of the gap thickness.
Figure 11B:
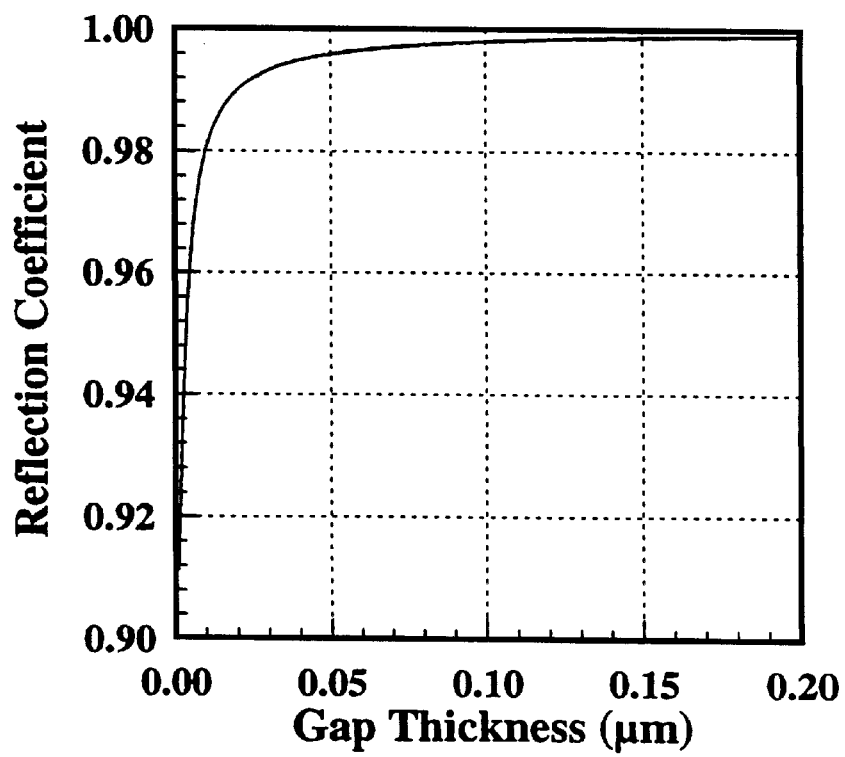

FIGS. 11a and 11b show the results of the calculated reflection coefficients for the steel-air-cast aluminum and steel-air-injected polymer as a function of the gap thickness. They indicate that ultrasonic reflection coefficient is very sensitive to the gap size of the order of tenths of a micron, thus it can be used to monitor the gap development.

The gap detected by ultrasound represents a physical gap that prevents the transfer of energy in terms of stress waves. On the other hand, since, in the die casting or injection molding processes, thermal energy is mainly transferred by conduction, the range of gaps which can be detected by ultrasound may present significant resistance to heat transfer. In other words, such a gap makes the cooling inefficient and ultrasonic detection of the gap formation is a very sensitive, reliable and important approach.

In addition, ultrasonic monitoring can be also performed at the gap and runner locations during the die casting and injection molding.

During the manufacturing of industrial materials, temperature is one of the important parameters which can determine the quality of the products and the production efficiency. For instance, the cooling rate and cooling line design are the key factors during the design of the die and the mold. Although standard thermocouples can be used to measure the temperature for the die casting of metals, polymer injection molding and extrusion processes, however, it is much desirable that the measurement of temperature can be simultaneously performed together with those for the flow front, gap development and viscosity monitoring and at the same location, thus the relation between the temperature, cooling mechanism, gap development and viscosity can be found easily.

Figure 12:
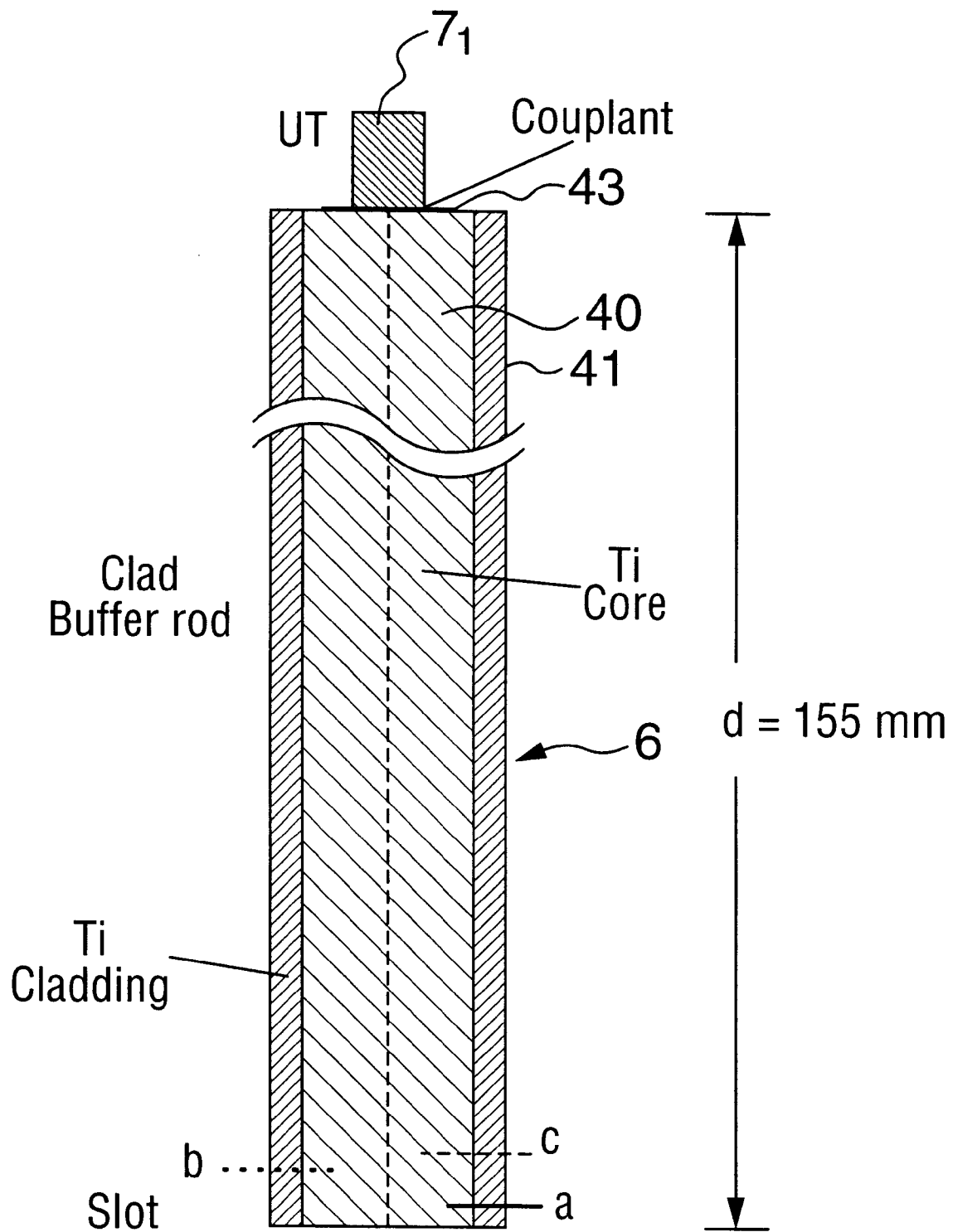
FIG. 12 is a schematic of the temperature measurement using the ultrasonic waveguides in which three slots; namely a, b and c, are created in the core region.
Figure 13:
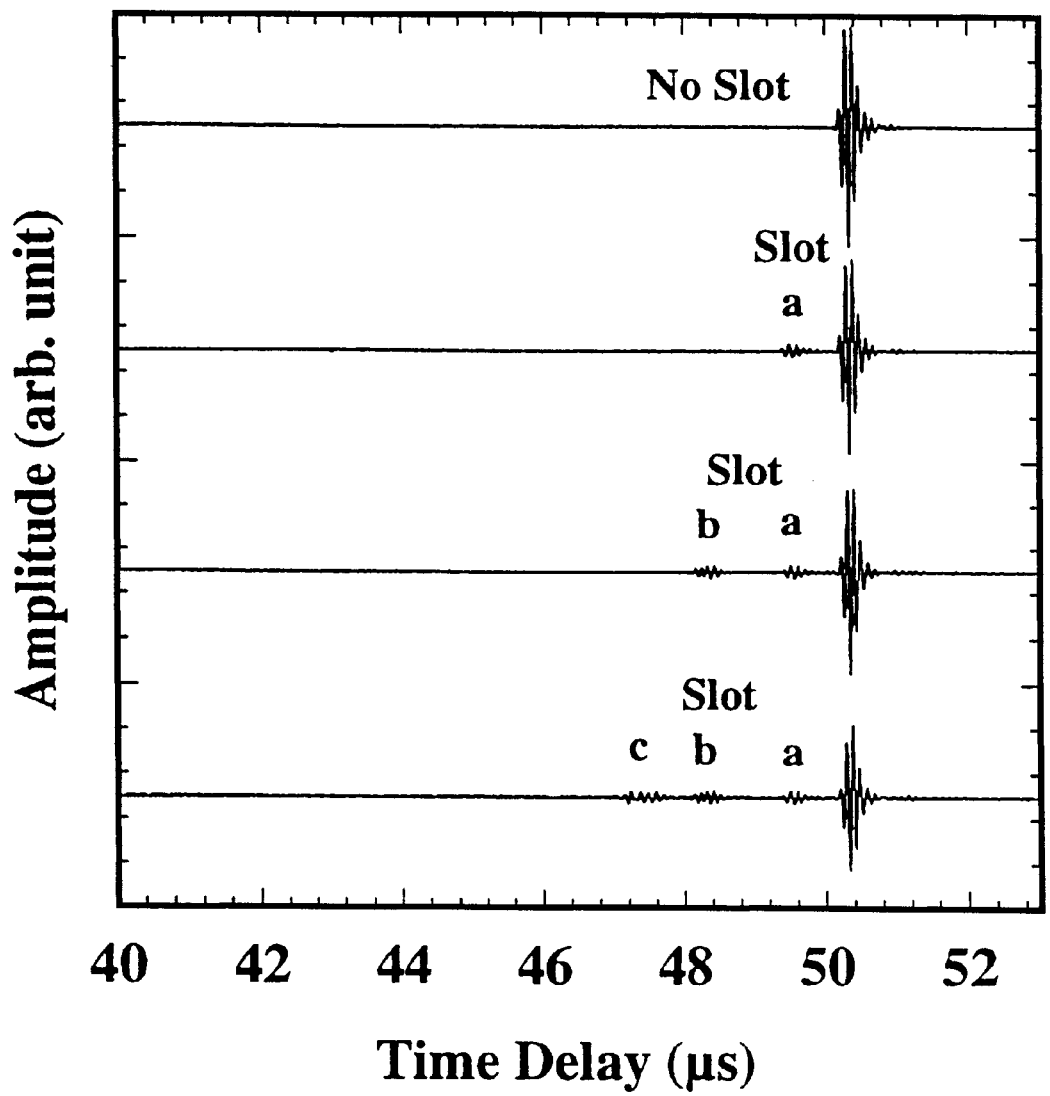
FIG. 13 shows the reflected ultrasonic longitudinal wave signals corresponding to the reflections from the end of an ultrasonic waveguide and three slots; a, b and c, shown in FIG. 12.

FIG. 12 shows a schematic of the temperature measurement using a clad buffer rod 6 with a central core 40 and an outer sleeve cladding 41. An ultrasonic transducer $7_1$ is located at the free end of the buffer rod 6 and is coupled to it by couplant 43. Three slots a, b and c, are created in the core 40 and the reflected 20 MHz ultrasonic longitudinal wave signals corresponding to the reflections from the end of this buffer rod 6 and these three slots are shown in FIG. 13. Slots a, b and c are created sequentially.

The depth of each slot can be adjusted to have the desired amount of reflection. Since the ultrasonic velocity in the buffer rod 6 is a function of temperature and the distance between the slot and the end of the buffer rod is known, one can monitor the time delay between the reflected ultrasonic signals at the end of the buffer rod 6 and that at the slot location, e.g. a, then the velocity which is directly related to the average temperature in this particular location zone can be derived. Similarly, the average temperature at the zone between a and b, and also b and c can be obtained if the reflected ultrasonic signals at these locations are used. This temperature information can be used to design the cooling channel layout and cooling rate which affect the production rate and quality of the products.

In addition, the measured temperature at location a may be treated as the surface temperature of the part and the temperature difference between the locations a and b or b and c may be used to obtain the heat flux radiating outwardly from the monitored part. Since the ultrasound may penetrate through the cast, molded or extruded part, the average ultrasonic velocity which relates to the average temperature of the part can be obtained. Using the three sets of information; namely surface temperature, heat flux radiating outwardly from the part and the averaged temperature of the part one can obtain the temperature profile of the manufactured part, an important parameter for the optimization of the manufacturing process.

FIG. 13 shows that even with the presence of the three slots, the reflected ultrasonic signal at the end of the buffer rod decreases a little but can still be used for the monitoring of the flow front, gap development and viscosity because these slots do not generate undesired spurious signals. This means that slots can be created in the buffer rods 6 shown in FIGS. 1, 4 and 7, and the monitoring of the temperature, flow front, gap development and viscosity can be performed simultaneously and at the same buffer rod location.

For squeeze casting and semi-solid casting which are two modern types of die casting processes the above mentioned flow front, gap development and temperature monitoring using ultrasound may be performed as well. Squeeze casting refers to a process in which liquid metals are cast without turbulence and gas entrapment and during the solidification cycle high pressure is maintained to yield high quality heat treatable components. In order to reduce the gas entrapment and turbulence the shot sleeve is oriented vertically and upward injection is applied. Such mechanical modification does not affect the ultrasonic measurements at all. During semi-solid casting the injected material has the consistency of a toothpaste. Since there exists an impedance mismatch between the steel which is the material for die or buffer rod and the semi-solids, at this interface the reflected ultrasonic echo may be used to perform the flow front, gap development and the temperature monitoring.

The buffer rods shown in FIGS. 1, 4, 7 and 12 may be clad ultrasonic waveguides which consist of a core 40 and a cladding 41. The ultrasonic waves are guided in the core.

For certain situations the cooling system for the buffer rod shown in FIGS. 1, 4, 7 and 12 may not be convenient, for instance, due to size limitations, therefore UTs made of high Curie temperature materials directly fabricated on top of the buffer rod are desired. Sol-gel fabricated lead zirconate titanate thin piezoelectric films have been directly deposited on metal coated glass optical fibers for devices used for medical and telecommunication application. Since lead zirconate titanate can only work properly below 150° C. due to low Curie temperature (<350° C.), another embodiment of uses a sol-gel method to produce piezoelectric UTs of high Curie temperature (>350° C.) and these UTs have a thickness of more than 100 µm because of the preferred operation frequency, which is commonly in the range of 0.5–30 MHz. The piezoelectric materials can be lithium tantalate with a Curie temperature of 600° C. or lithium niobate with a Curie temperature of 1200° C.

These thick film UTs can be fabricated by dispersing solid and very fine piezoelectric particles into the sol-gel solution, and this dispersed solution is then directly coated at the end of the buffer rod. Thickness can be increased by using multiple coatings. Coated films need sintering and electrical poling processes to become piezoelectric UTs.

The piezoelectric UTs with high Curie temperatures (>350° C.) can be directly deposited onto the external wall of shot sleeve, die, mold or the extruder machines which are commonly made of steel. In this case, the wall serves as the waveguide through its thickness. However, in such a configuration the temperature profile can not be measured due to lack of slots shown in FIG. 12. In principle, the wall of the shot sleeve shown in FIG. 1, die or mold shown in FIG. 7 or the extruder machines shown in FIG. 4 suffers higher ultrasonic loss than the buffer rod for which a core material with a low ultrasonic loss can be selected. The advantage of this approach is that there is no need to drill a hole in the die, mold or extruder for the accommodation of the waveguide.

We claim:

1. An apparatus for monitoring a mass of molten material in a cavity, comprising:
    an array of buffer rods, each buffer rod having a proximal end extending into said cavity and a distal end extending outside said cavity;
    an ultrasonic transducer operable in the reflection mode mounted on the distal end of each said buffer rod;
    means for energizing said transducers so that they emit pulses of ultrasonic energy into the molten material through said buffer rods;
    receiving means for receiving return pulses from said transducers;
    axially spaced reflection means in said buffer rods at the proximal end thereof for reflecting pulses emitted by said transducers; and
    a computer for analyzing said return pulses to derive data therefrom pertaining the state of the molten material, said computer being programmed to calculate the velocity of said return pulses reflected from said axially spaced means and derive therefrom the temperature of said buffer rods between said axially spaced means.

2. An apparatus as claimed in claim 1, further comprising a multiplexer for sequentially connecting said respective transducers to said energizing means and said receiving means.

3. An apparatus as claimed in claim 1, wherein each said buffer rod comprises a central axial core surrounded by a cladding sleeve.

4. An apparatus as claimed in claim 1, further comprising a cooling jacket surrounding each said transducer at the distal end of said buffer rods.

5. An apparatus as claimed in claim 1, wherein an ultrasonic coupling material is located between each said transducer and the distal end of each buffer rod.

6. An apparatus as claimed in claim 1, wherein said ultrasonic transducers are operable in the longitudinal wave mode.

7. An apparatus as claimed in claim 1, wherein said ultrasonic transducers are operable in the shear wave mode.

8. An apparatus as claimed in claim 1, wherein said computer is programmed to derive from said travel time of said return pulses additional information pertaining to surface disturbance arid solidification of the molten material.

9. An apparatus as claimed in claim 1, wherein said computer is programmed to additionally derive the viscosity of the molten material from said travel time of said return pulses and the degree of their attenuation.

10. An apparatus as claimed in claim 1, wherein said computer is programmed to additionally derive from the amplitude variation of the return pulses, information pertaining to the flow and gap development of the molten material.

11. An apparatus as claimed in claim 1, wherein said axially spaced means are transverse slots.

12. An apparatus as claimed in claim 1, wherein said respective ultrasonic transducers are directly fabricated onto the distal ends of the buffer rods.

13. An apparatus as claimed in claim 12, wherein said ultrasonic transducers are sol-gel fabricated thick film piezoelectric transducers.

14. An apparatus for measuring the temperature of a mass of molten material in a cavity, comprising:
    at least one buffer rod, the or each buffer rod having a proximal end for extending into the cavity and a distal end for extending outside the cavity;
    an ultrasonic transducer operable in the reflection mode mounted on the distal end of the or each said buffer rod;
    means for energizing the or each said transducer to emit pulses of ultrasonic energy into die molten material through the or each said buffer rod;
    receiving means for receiving return pulses from the or each said transducer; and
    axially spaced reflection means in the or each said buffer rod at the proximal end thereof for reflecting pulses emitted by the or each said transducer to permit the temperature of the or each said buffer rod between said axially spaced means to be derived from the travel times of the return pulses reflected from said axially spaced means.

15. An apparatus as claimed in claim 14, wherein said axially spaced means are transverse slits.

16. An apparatus as claimed in claim 15, comprising at least three axially spaced said transverse slits.

17. An apparatus as claimed in claim 16, wherein said buffer rods comprise a central axial core surrounded by a cladding sleeve.

18. An apparatus as claimed in claim 17, wherein said transducers are directly fabricated onto the distal end of said respective buffer rods.

19. An apparatus as claimed in claim 18 wherein said transducers comprise piezo-electric particles dispersed in a sol-gel solution coated onto the distal ends of said buffer rods.

20. An apparatus as claimed in claim 19, wherein said piezo-electric particles are selected from the group consisting of lithium tantalate and niobium tantalate.

21. An apparatus as claimed in claim 14, comprising an array of said buffer rods.

* * * * *